March 26, 1940. M. REUTER Plant Pat. 371
DELPHINIUM
Filed Aug. 4, 1939
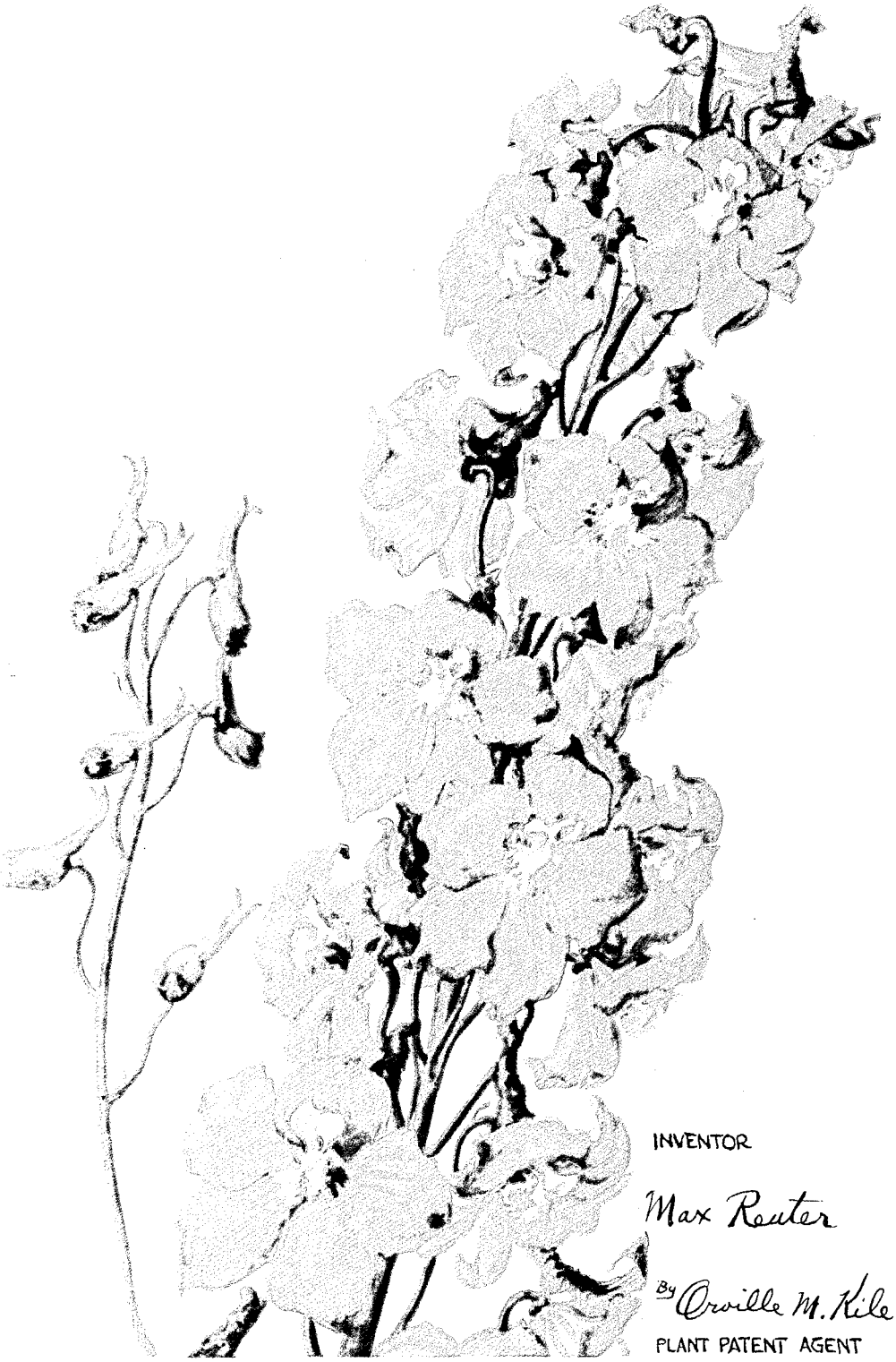
INVENTOR
Max Reuter
By Orville M. Kile
PLANT PATENT AGENT Patented Mar. 26, 1940

Plant Pat. 371

UNITED STATES PATENT OFFICE

371

DELPHINIUM

Max Reuter, Blue Point, N. Y.

Application August 4, 1939, Serial No. 288,425

1 Claim. (Cl. 47—60)

My new variety pertains to hybrid perennial delphiniums of the *belladonna* type and is the result of direct efforts to improve the strength and vigor of the variety Statuare-Rude. During the years 1925–28 I made a large number of crosses between the semi-double Statuare-Rude as the seed parent, and the double American Hybrid as the pollen parent and finally discovered my present variety as one of the seedlings resulting from these crosses. I have since propagated this variety by means of division and cuttings and have found the unusual characteristics of the variety to be firmly fixed. No seeds have ever been produced by this new variety so all propagation must be asexual.

Some of the outstanding features which in combination readily distinguish my new variety from other known varieties are as follows:

The larger number of flowers in a raceme or "spike"; the greater lasting quality of its flowers; its complete immunity to mildew; its entire lack of seeds; its greater freedom of blooming; its hardiness; and its resistance to heat, frost and dry weather together with its continuous production throughout the season.

My new variety resembles the variety Belladonna Improved more than any other known to me. Its distinctive qualities would, therefore, probably be best shown by a comparison of the new variety with Belladonna Improved.

The greatest point of difference is the length of the so-called spike (or raceme) and the number of blossoms produced. Racemes of my new variety are two to three times longer than those of Belladonna Improved and usually contain from 25 to 30 blossoms each. A greater number of side branches are produced and there are four complete crops of blossoms per season. The combination of these features makes possible the production of four to six times as many flowers as Belladonna Improved or other similar varieties.

The racemes on a one-year plant are about 16 inches in length and the stems of such a plant never exceed one-fourth inch in diameter. This is much longer and more slender than those of Belladonna Improved. The stems are also straighter, more pliable and consequently more graceful in my new variety.

Although all flowers in a single raceme open within the same day, the flowers last much longer than in other varieties, which feature makes this variety especially desirable as a cut flower.

The flowers of my new variety are larger and the color shadings richer and more pronounced than those of Belladonna Improved. The spurs are double-pointed rather than single as in Belladonna Improved.

Plants of this variety have been one hundred percent immune to mildew while Belladonna Improved and other varieties growing under the same conditions have been affected by it. The variety is very hardy, being resistant to frost, heat and drought; and is not subject to infestation by bees. The plants do not grow so tall as those of *Belladonna*, but produce a greater number of side shoots, resulting in a bushier growth.

The original illustrations accompanying this application show in approximately their true colors, the top portion of a raceme of flowers of this new variety, together with a side spray or raceme of buds, showing their relative development. This portion of the flower raceme represents about one-half its whole length, which would in its entirety carry about 30 blossoms.

Following is a detailed description of this new variety of delphinium, in which color plate designations indicate Ridgway's Color Standards and Nomenclature. Where plates are not indicated, the ordinary dictionary term is intended.

*The plant*

Growth: Fast and steady grower throughout the season. Branching and bushy, attaining a height of not more than 3 feet. Hardy and prolific, not materially affected by hot or dry weather and can stand considerable frost.

Blooming: Very free blooming, producing four to six times as many flowers as similar varieties. Each plant produces four complete crops of flowers per season. These are produced on showy racemes from 12 to 16 inches long and with several lateral racemes on each stalk. All the blossoms on a raceme open within the same day. Apparently the blooming strength is centered, because the lateral racemes open less rapidly than is usually the case with similar varieties.

Disease Resistance: Completely immune to mildew which is the worst disease enemy of delphiniums.

Insect Resistance: The spurs are not infested by bees as they are in many similar varieties.

Roots: Hardy; fibrous.

Foliage: Erect; normal quantity, extending throughout the entire season.

*Leaves.*—Shape—flat; palmately divided into 3 to 7 lobes, each lobe of which is usually trifid. This corresponds very closely to Belladonna Improved. Color—upper surface between Cress Green and Dark Cress Green (Plate XXXI); under surface, Light Elm Green (Plate XVII). Aspect—glabrous; ribs and veins prominent; upper surface glossy; under surface dull. Rachis—slightly darker and heavier than pedicels; grooved on upper side; slightly dilated at base.

*Stems.*—Slender; strong; straight; pliable; graceful; round; glabrous; approximately Parrot Green (Plate VI), with length about equal to length of raceme which it bears. Pedicels and bracteoles approximately same color as stems.

*The flower*

Bud:

*Color.*—Light Viridine Yellow (Plate V), tipped with Cosse Green (Plate V). When opening they assume the blue color at the tip end first.

*Size.*—At the stage shown the buds are about ⅜ inch to ½ inch in length.

Blossom:

*Arrangement.*—Flowers are arranged on long showy racemes containing from 20 to 30 blossoms, this being at least two or three times as many as are usually found on similar varieties.

*Opening.*—All the blossoms in one raceme open within the period of one day. The two to four lateral racemes are very small when the central one is in full bloom.

*Size.*—The entire blossom attains a size up to 2 inches in diameter.

*Form.*—The flower is composed of a very small true flower surrounded by five large petal-like sepals, the posterior one of which extends into a spur. True flowers—the true flower is composed of two spreading upper petals with two smaller petals below them, the stamens and pistils hidden by the upper two. Color—the two lower petals are white; the two upper petals are white edged with a trace of Lavender (Plate XXXVI) and with a central spot of Wax Yellow (Plate XVI) which is composed of hairy projections. These yellow spots are much smaller than in the Belladonna Improved, and the hairy projections are not so long. Stamens—short and curved. Filaments white. Anthers black. Carpels—three; white; devoid of seed.

*Sepals.*—Five; large; petal-like, the posterior one extended into a spur. Color—light Cadet Blue to Clear Cadet Blue (Plate XXI). Spurs—length about equal to width of petal-like sepal; double-pointed rather than the usual single point; Deep Dull Bluish Violet (Plate XXIV).

Having thus disclosed my invention, I claim:

A new and distinct variety of perennial hybrid delphinium with qualities in combination substantially as shown and described, characterized particularly by its prolific production of large, richly colored flowers of the belladonna type; its racemes from 12 to 16 inches long, flowers of which all open in a single day; the lasting quality of its flowers; the absence of seeds; its thin, pliable stems; its immunity to mildew; its resistance to adverse weather conditions and freedom from infestation by bees; its low, bushy growth throughout the season; and its habit of producing four crops of bloom during a season.

MAX REUTER.